(12) United States Patent
Gronheid et al.

(10) Patent No.: US 10,048,212 B2
(45) Date of Patent: Aug. 14, 2018

(54) QUALITY ASSESSMENT OF DIRECTED SELF-ASSEMBLING METHOD

(71) Applicants: IMEC VZW, Leuven (BE); Katholieke Universiteit Leuven, KU LEUVEN R&D, Leuven (BE)

(72) Inventors: Roel Gronheid, St. Agatha Rode (BE); Lieve Van Look, Leuven (BE); Paulina Alejandra Rincon Delgadillo, Leuven (BE)

(73) Assignee: IMEC VZW, Leuven (BE)

( * ) Notice: Subject to any disclaimer, the term of this patent is extended or adjusted under 35 U.S.C. 154(b) by 432 days.

(21) Appl. No.: 14/673,986

(22) Filed: Mar. 31, 2015

(65) Prior Publication Data

US 2015/0276624 A1 Oct. 1, 2015

(30) Foreign Application Priority Data

Mar. 31, 2014 (EP) .................................... 14162688

(51) Int. Cl.
| | |
|---|---|
| *G06F 11/30* | (2006.01) |
| *G21C 17/00* | (2006.01) |
| *G01N 21/956* | (2006.01) |
| *G01N 21/47* | (2006.01) |
| *G03F 7/00* | (2006.01) |

(52) U.S. Cl.
CPC ....... *G01N 21/95607* (2013.01); *G01N 21/47* (2013.01); *G03F 7/0002* (2013.01); *G01N 2201/12* (2013.01)

(58) Field of Classification Search
CPC .............................................. G01N 21/95607
USPC .......................................................... 702/182
See application file for complete search history.

(56) References Cited

U.S. PATENT DOCUMENTS

| | | | |
|---|---|---|---|
| 7,289,213 B2 | 10/2007 | Mieher et al. | |
| 7,940,386 B1 | 5/2011 | Bevis | |
| | (Continued) | | |

OTHER PUBLICATIONS

Delgadillo, Paulina A. Rincon et al., "All Track Directed Self-Assembly of Block Copolymers: Process Flow and Origin of Defects", Proceedings of SPIE—The International Society for Optical Engineering, vol. 8323, published 2012, pp. 83230D-1-83230D-9.

*Primary Examiner* — Igwe U Anya
(74) *Attorney, Agent, or Firm* — McDonnell Boehnen Hulbert & Berghoff LLP

(57) ABSTRACT

A method for evaluating the quality of a directed self-assembling method used for generating directed self-assembling patterns. The method for evaluating comprises obtaining at least one set of parameter values for a parameterized set of processing steps and material properties characterizing the directed self-assembling method, thus characterizing a specific directed self-assembling method used for generating a directed self-assembled pattern. The method furthermore comprises obtaining a scattered radiation pattern on the directed self-assembled pattern obtained using the directed self-assembling method characterized by the set of parameter values, thus obtaining scattered radiation pattern results for the directed self-assembled pattern. The method furthermore comprises determining based on the scattered radiation pattern results a qualification score and correlating the qualification score with the set of parameter values.

18 Claims, 8 Drawing Sheets

(56) References Cited

U.S. PATENT DOCUMENTS

| | | | | |
|---|---|---|---|---|
| 2003/0201410 | A1* | 10/2003 | Nagamura | G01N 21/8806 250/559.45 |
| 2008/0024766 | A1 | 1/2008 | Mieher et al. | |
| 2008/0106729 | A1* | 5/2008 | Vuong | G01N 21/4788 356/73 |
| 2010/0057391 | A1* | 3/2010 | St. Pierre | H01L 22/14 702/81 |
| 2011/0285839 | A1* | 11/2011 | Kotaki | G06T 7/001 348/80 |
| 2013/0144560 | A1* | 6/2013 | Pisarenco | G01N 21/47 702/189 |
| 2014/0198975 | A1* | 7/2014 | Nakagaki | G01N 23/2251 382/149 |
| 2014/0202984 | A1* | 7/2014 | Quesada | G03F 7/0002 216/11 |

* cited by examiner

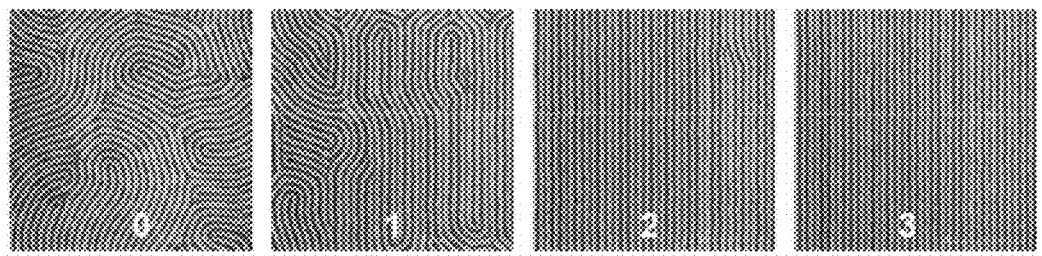
FIG. 1 – Prior Art
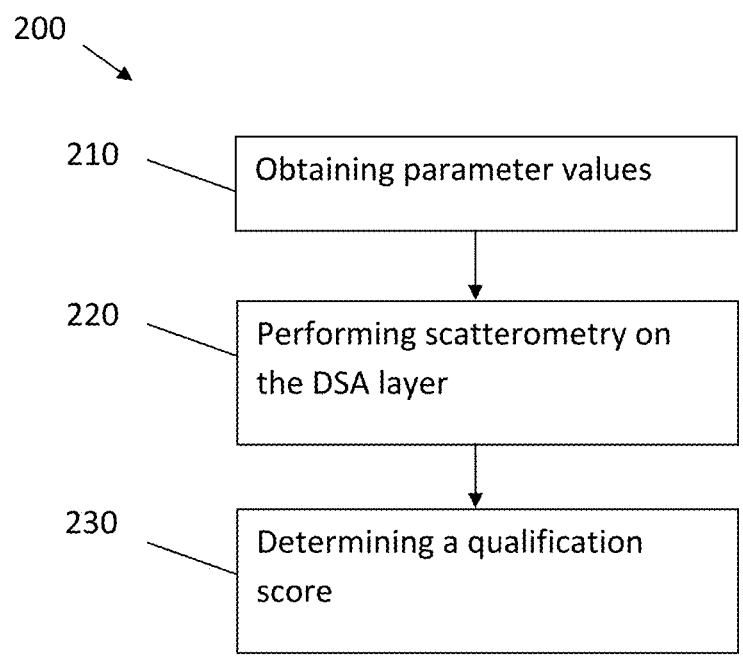
FIG. 2

|  | YS based scoring W425 | | | | |
| --- | --- | --- | --- | --- | --- |
|  | 82 | 83 | 84 | 85 | 86 |
| Ref_No_Order | 0.005 | 0.005 | 0.005 | 0.005 | 0.005 |
| CD1 | 0.005 | 0.007 | 0.011 | 0.005 | 0.005 |
| CD2 | 0.036 | 0.036 | 0.036 | 0.025 | 0.021 |
| CD3 | 0.036 | 0.036 | 0.037 | 0.037 | 0.033 |
| CD4 | 0.036 | 0.037 | 0.037 | 0.037 | 0.036 |
| CD5 | 0.014 | 0.037 | 0.037 | 0.037 | 0.036 |
| CD6 | 0.005 | 0.035 | 0.037 | 0.037 | 0.036 |
| CD7 | 0.022 | 0.012 | 0.029 | 0.036 | 0.033 |
| CD8 | 0.037 | 0.005 | 0.009 | 0.031 | 0.025 |
| CD9 | 0.021 | 0.017 | 0.005 | 0.014 | 0.014 |

FIG. 3

|  | Manual scoring | | | | |
| --- | --- | --- | --- | --- | --- |
|  | 82 | 83 | 84 | 85 | 86 |
| Ref_No_Order | 0 | 0 | 0 | 0 | 0 |
| CD1 | 0 | 0 | 0 | 1 | 0 |
| CD2 | 3 | 2 | 3 | 1 | 1 |
| CD3 | 3 | 3 | 3 | 3 | 1 |
| CD4 | 2 | 3 | 3 | 3 | 2 |
| CD5 | 1 | 3 | 3 | 3 | 2 |
| CD6 | 0 | 2 | 3 | 3 | 2 |
| CD7 | 1 | 0 | 1 | 2 | 1 |
| CD8 | 2 | 0 | 0 | 1 | 1 |
| CD9 | 1 | 1 | 0 | 1 | 1 |

QUALITY ASSESSMENT OF DIRECTED SELF-ASSEMBLING METHOD

CROSS-REFERENCE TO RELATED APPLICATION

This application claims priority to European Patent Application No. 14162688.7 filed on Mar. 31, 2014, the contents of which are hereby incorporated by reference.

FIELD OF THE DISCLOSURE

The disclosure relates to the field of quality assessment of patterning techniques. More specifically it relates to a method and device for evaluating the quality of a directed self-assembling method used for generating directed self-assembling patterns.

BACKGROUND OF THE DISCLOSURE

Directed Self-Assembly (DSA) of block copolymers (BCP) using chemo-epitaxy is a patterning technique that allows the formation of regular gratings with resolutions below what is possible with current lithography tools. It makes use of spontaneous micro-phase separation of block copolymers (BCP). DSA is considered as one of the potential methods to obtain feature densities that cannot be obtained using actual optical techniques.

Optimally, the DSA technique used for generating particular gratings has a large processing window and is little or not sensitive to varying conditions. In order to define optimal materials, processing conditions and processing steps, the DSA technique typically at present is evaluated by studying gratings obtained with the DSA technique. More particularly, the order in the grating is qualified. The latter typically is done by manual classification of a series of Scanning Electron Microscopy (SEM) images of the grating, with a typical field-of-view of about 6 µm². For this manual classification, for example, use is made of a discrete scale from 0 to 3 describing the amount of order in the grating. By way of illustration, FIG. 1 illustrates SEM images of DSA gratings as used for classification. In this example, the left-most image of the grating would result in a score of 0 and the most right figure would result in a score of 3. The score 0 represents complete disorder, while the score 3 represents prefect order.

The scoring is a manual task and thus operator-dependent and furthermore is time-consuming. In addition, to keep the evaluation feasible, the area probed is limited, and therefore the tests may still depend on the exact location that was probed with SEM.

Therefore, there is still room for improvement in scoring methods and devices for scoring the quality of DSA patterns.

SUMMARY OF THE DISCLOSURE

Embodiments of the present disclosure provide an efficient way for evaluating a directed self-assembling method for generating directed self-assembling patterns.

One potential advantage of embodiments according to the present disclosure is that the speed for checking the quality (e.g., the process windows and the process sensitivities) of directed self-assembled patterns or the quality of particular methods for obtaining self-assembled patterns is high (e.g., compared to the existing methods based on SEM measurements). Another potential advantage of embodiments according to the present disclosure is that inspection for evaluating the quality of self-assembled patterns or methods of obtaining them can be performed in an automated or computer-implemented way. Generally, embodiments of the present disclosure help to obtain an objective quality parameter, and allow for a more streamlined and accurate evaluation/characterization. These and other objectives or advantages may be accomplished by a method and device according to the present disclosure.

The present disclosure relates to a method for evaluating the quality of a directed self-assembling method used for generating directed self-assembling patterns. In one example, the method includes obtaining at least one set of parameter values for a parameterized set of processing steps and material properties characterizing the directed self-assembling method, thus characterizing a specific directed self-assembling method used for generating a directed self-assembled pattern. In this example, the method also includes obtaining a scattered radiation pattern from the directed self-assembled pattern obtained using the directed self-assembling method characterized by the set of parameter values, thus obtaining scattered radiation pattern results for the directed self-assembled pattern. Further, this example method includes determining, based on the scattered radiation pattern results, a qualification score, and correlating the qualification score with the set of parameter values. The qualification score may be determined by a relative evaluation with an ideal situation.

Embodiments of the present disclosure may help to achieve one or more advantages, such as obtaining a high acquisition speed, sampling a large area of the DSA pattern, providing a continuous output scale, and fast and automated data processing.

Obtaining a scattered radiation pattern may comprise obtaining a scattered radiation pattern on a directed self-assembled pattern obtained by applying a directed self-assembling method characterized by the set of parameter values on a pattern comprising a number of induced defects, and wherein the determining a qualification score comprises determining a qualification score identifying a robustness of the directed self-assembling method to the induced defects in the pattern.

By making use of a pattern with a number of induced defects, the sensitivity to defects and the propagation of the DSA technique of such defects can be characterized and quantified. The latter provides a proper metric for fast evaluation of the DSA technique and its processing window.

The induced defects may include one or more of non-local or local pitch offsets, interruptions in the line patterns and local or non-local critical dimension (CD) bias.

The induced defects may be randomly distributed.

The induced defects may be systematically distributed. The induced defects may for example be distributed along a diagonal of the pattern.

The induced defects may be tuned in density. The induced defects may be tuned in strength. The induced defects may be introduced regularly. Such a regular introduction may be every predetermined number of lines.

The method may comprise obtaining a plurality of sets of parameter values for the parameterized set of processing steps and material properties, the plurality of sets of parameter values spanning a process window for the directed self-assembling method, performing the steps of obtaining a scattered radiation pattern and determining a qualification score for each of the sets of parameters, and evaluating the process window for the directed self-assembling method based on the obtained qualification scores through the process window.

It is an advantage of embodiments according to the present disclosure that process window analysis for a directed self-assembling method can be performed in an efficient and accurate way. It is an advantage that the technique disclosed herein allows obtaining similar results as obtained with SEM measurements in a shorter time scale. It is an advantage of embodiments according to the present disclosure that they can help speed up progress in DSA research.

Determining, based on the scattered radiation pattern results, a qualification score may comprise performing a normalization of the scattered radiation pattern results.

Performing a normalization may comprise normalizing the scattered radiation pattern results using an analysis of scanning electron microscopy measurements of the self-assembled patterns. It is an advantage of embodiments according to the present disclosure that, by using normalization, an accurate metric is obtained that allows accurate interpretation of the quality of the process. It is an advantage of embodiments according to the present disclosure that a good reproducibility is obtained. It is an advantage of embodiments according to the present disclosure that the scattered radiation pattern technique is easy to implement and does not require knowledge of n, k, and the pitch.

The method furthermore may comprise comparing the qualification score correlated with the set of parameters with a qualification score obtained earlier in time for the set of parameter values, and evaluating based on the comparing whether the directed self-assembling method needs to be amended.

Comparing the qualification may comprise comparing with a reference, such as for example a look up table, comprising previously recorded qualification scores correlated with specific sets of parameter values. Comparing may be performed after or while normalizing. The qualification scores may be relative numbers.

The method may comprise obtaining a directed self-assembled pattern by applying a directed self-assembling method characterized by the set of parameter values on a pattern comprising a number of induced defects.

The present disclosure also relates to a non-transitory computer program product for, when run on a processing unit, performing a method for evaluating as described above.

The present disclosure furthermore relates to a data carrier comprising such a computer program product or the transmission thereof over a local or wide area network.

The present disclosure also relates to a system storing a set of comparative data, the comparative data correlating sets of parameter values for a parameterized set of processing steps and material properties characterizing a directed self-assembling method on the one hand and a qualification score based on scattered radiation pattern results obtained from a scattered radiation pattern technique on a directed self-assembled pattern obtained using the directed self-assembling method characterized by the set of parameter values.

It is an advantage of such systems that they allow proper evaluation of processes performed on site. Such a check provides information not only on the DSA method used, but also may be indicative of another change in the processing chain of materials that influences the DSA method. In this way, fast identification of process changes can be performed, resulting in a faster identification of problems and less down time of processing systems.

In the system, the comparative data may correlate sets of parameter values for a parameterized set of processing steps and material properties characterizing a directed self-assembling method on the one hand and a qualification score based on scattered radiation pattern results obtained from a scattered radiation pattern technique on a directed self-assembled pattern obtained using the directed self-assembling method characterized by the set of parameter values and applied to a pattern comprising a number of induced defects.

The comparative data may be normalised based on scanning electron microscopy reference data.

The system furthermore may comprise a non-transitory computer program product as described herein.

The present disclosure also relates to a set of comparative data, the comparative data correlating sets of parameter values for a parameterized set of processing steps and material properties characterizing a directed self-assembling method on the one hand and a qualification score based on scattered radiation pattern results obtained from a scattered radiation pattern technique on a directed self-assembled pattern obtained using the directed self-assembling method characterized by the set of parameter values.

The comparative data may correlate sets of parameter values for a parameterized set of processing steps and material properties characterizing a directed self-assembling method on the one hand and a qualification score based on scattered radiation pattern results obtained from a scattered radiation pattern technique on a directed self-assembled pattern obtained using the directed self-assembling method characterized by the set of parameter values and applied to a pattern comprising a number of induced defects.

Particular and example aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE DRAWINGS

FIG. 1 illustrates the manual scoring of DSA gratings according to a prior art solution.

FIG. 2 illustrates an example method for evaluating the quality of a DSA method used for generating DSA patterns according to an embodiment of the present disclosure.

FIG. 3 illustrates the qualification scores obtained using a method in accordance with embodiments of the present disclosure.

FIG. 4 shows manual scoring of the order in the same DSA gratings as FIG. 2 where the scoring is performed based on a conventional method based on SEM.

Figure 5:
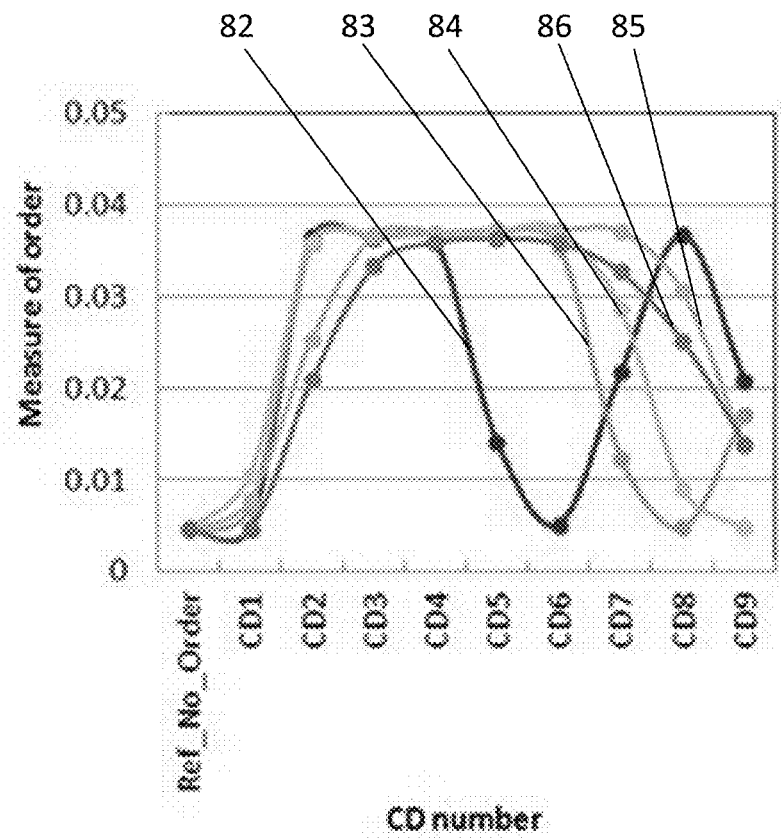
FIG. 5 shows the plotted data of FIG. 3.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the elements or steps listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices that include only components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects may lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Where in embodiments according to the present disclosure reference is made to a directed self-assembling (DSA) method, reference is made to a method making use of a phenomenon where components of a pattern assemble themselves spontaneously on the substrate to form a pattern.

Where in embodiments of the present disclosure reference is made to a guiding pattern, reference is made to a pattern that is used for performing a self-assembling method In a first aspect, the present disclosure relates to a method for evaluating the quality of a directed self-assembling (DSA) method used for generating directed self-assembling patterns. By way of illustration, FIG. 2 illustrates the different steps or processes of the evaluation method 200. According to embodiments, a block 210 corresponds to obtaining at least one set of parameter values for a parameterized set of processing steps and material properties characterizing the directed self-assembling method, thus characterizing a specific directed self-assembling method used for generating a directed self-assembled pattern. At a block 220, a scattered radiation pattern technique is performed on the directed self-assembled pattern obtained using the directed self-assembling method characterized by the set of parameter values, thus obtaining scattered radiation pattern results for the directed self-assembled pattern. At a block 230, based on the scattered radiation pattern results, a qualification score is determined and the qualification score is correlated with the set of parameter values. In some particular embodiments, the method is used for evaluating the processing window of the DSA method applied and its sensitivity to errors, e.g., in the pattern to be generated. In some other embodiments, the method is used as a standard characterization and/or checking routine for evaluating changes in the DSA method applied. For optimizing evaluation of the sensitivity to errors, the method may comprise obtaining results for a DSA method applied to a pattern, wherein intended defects are introduced and evaluating the resulting grating. By way of illustration, embodiments of the present disclosure not being limited thereby standard and optional features for standard and optional steps of the method 200 will now be further discussed below, with reference to FIG. 2.

In embodiments of the present disclosure, the block 210 may include selecting the parameters which characterize the DSA method. These parameters may comprise parameters directly defining the DSA method used, such as for example dose and/or focus, but also may include other parameters more indirectly influencing the DSA process, such as for example parameter further defining the processing conditions (e.g., temperature and the like), parameters regarding the pattern to be made, etc. In some embodiments, specifically the parameters involved in defect growth in DSA may be screened, as it may be useful to learn the sensitivity of the method with respect to defect growth. One of the controllable DSA parameters may also be the DSA chemicals that are used. Embodiments of the present disclosure can be used for determining differences in DSA patterning characteristics for different block copolymer (BCP) samples.

The speed of the method, comprising selecting the parameters and afterwards giving a qualification score to the resulting DSA patterns typically is high as the process typically is automated. Therefore fast screening of the different parameters is possible. Since the screening can be done faster, a broader screening is possible than with SEM analysis within the same time window.

In embodiments of the present disclosure, at the block 220, the obtaining a scattered radiation pattern, is performed using an angle-resolved polarized reflectometry based scatterometer. In this example, it thereby is an advantage that a large area can be scanned, therefore being more representative for defects occurring on the mask. The field of view of the scatterometer is thus much larger than the field of view of a SEM image which has a typical field of view of 6 $\mu m^2$. To obtain substantially the same information, the method based on the scattered radiation pattern technique according to the present disclosure takes a measurement and processing time of about 10 minutes compared to 4 hours being the measurement and processing time required when using SEM.

In embodiments of the present disclosure at the block 230 the scatterometer helps to qualify the order in gratings produced by DSA thus resulting in a qualification score. As will be described further, in some embodiments, the qualification is made for a DSA method applied to a pattern with induced defects, thus identifying how resistant the DSA method is to defects in the pattern. In embodiments of the present disclosure a grating qualification score is computed based on the light diffracted by the gratings.

In embodiments of the present disclosure, repetition of the block 210 for defining a set of parameter values, the block 220 for obtaining a scattered radiation pattern, and the block 230 for determining the qualification score can be used for performing process window analysis on DSA gratings. By determining the qualification score for a number of different processing conditions, an analysis of the process window can be made.

It is an advantage of embodiments of the present disclosure that the method can be performed in an automated way. Furthermore it is an advantage of such an automated analysis that a more objective analysis may be obtained.

By way of illustration, in a first example the automated and manual scoring of 50 DSA gratings is compared, wherein two parameters determining defect growth are varied, such as the pitch and the width of the pattern. The results (the qualification scores) of the automated technique based on a scattered radiation pattern technique according to an embodiment of the present disclosure are illustrated in FIG. 3. The results of the manual technique are shown in FIG. 4. As can be seen from FIG. 3 and FIG. 4, there is a good correspondence between the manual and the automated technique. Some differences may still occur because the scattered radiation pattern based technique averages over an area which is much larger, for example, 200 times larger than the SEM based technique, or 1600 $\mu m^2$ compared to 6 $\mu m^2$ for the SEM based technique, for instance. Thereby the qualification score is an averaging result over the larger area. Therefore, as illustrated by the present example, the scattered radiation pattern based technique delivers a qualification score that is less location dependent than the SEM based technique. As discussed above, since the scattered radiation pattern based technique is an automated technique, the scattered radiation pattern based technique also delivers a qualification score that is less operator dependent and faster than the SEM based technique. As the resulting qualification scores are continuous (instead of discrete in the manual scoring case), this allows for a better understanding of the observed trends, making it easier to detect local maxima and minima. As an example, the qualification scores obtained from the scattered radiation pattern based technique, according to an embodiment of the present disclosure, are plotted in FIG. 5. The graphs in FIG. 5 show the qualification score as function of the CD.

Figure 6:
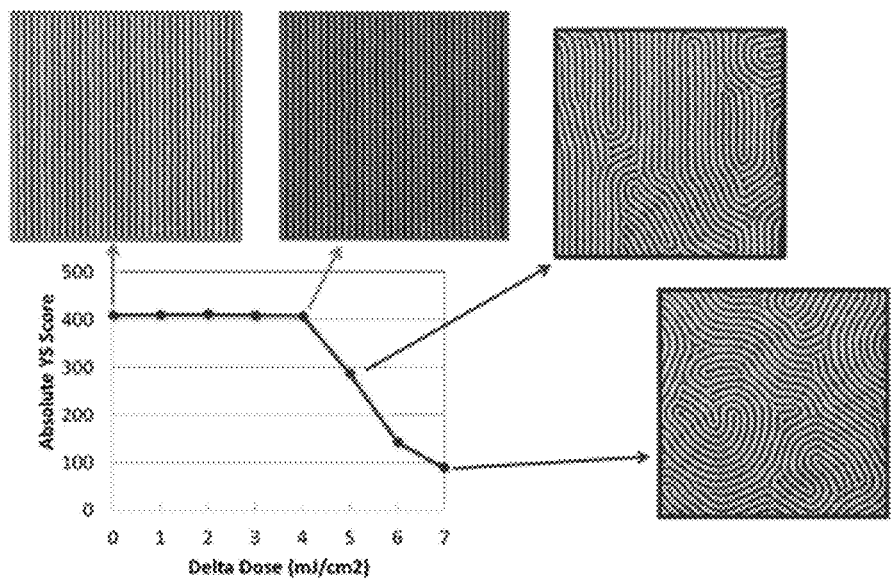
FIG. 6 shows a non-normalized qualification score as a function of a dose, wherein the score is obtained using a method according to the present disclosure.

By way of illustration, in a second example the qualification scores are obtained for a set of DSA patterns obtained by a DSA method wherein a different DSA dose is used for each DSA pattern. This is illustrated in FIG. 6. The SEM image of three DSA patterns is shown. Also a graph with the qualification score versus the DSA dose is shown. It is clear that a high qualification score corresponds with a high order in the grating and that a low qualification score corresponds with a low order in the grating.

In a number of particular embodiments, the present disclosure also relates to a technique for benchmarking DSA methods based on their sensitivity to defects in the guiding pattern of the pattern to be made by DSA. In such embodiments, the block 220 may comprise performing scatterometry on a directed self-assembled (DSA) pattern. The DSA pattern is obtained by applying a DSA method characterized by a set of parameter values on a pattern comprising a number of induced defects. The set of parameter values is defined at the block 210. Determining a qualification score comprises determining a qualification score identifying a robustness of the directed self-assembling method to the induced defects in the pattern. Other design characteristics which might be screened are critical dimension (CD) and programmed defects.

In an example embodiment, defects of various sizes and types are designed into the pattern. These defects may cause the DSA process to break down and induce patterning imperfections. Several types of defects are created in the grating to locally disturb the pattern. These defects may include for example defects illustrated by FIGS. 9-12.

Figure 9:
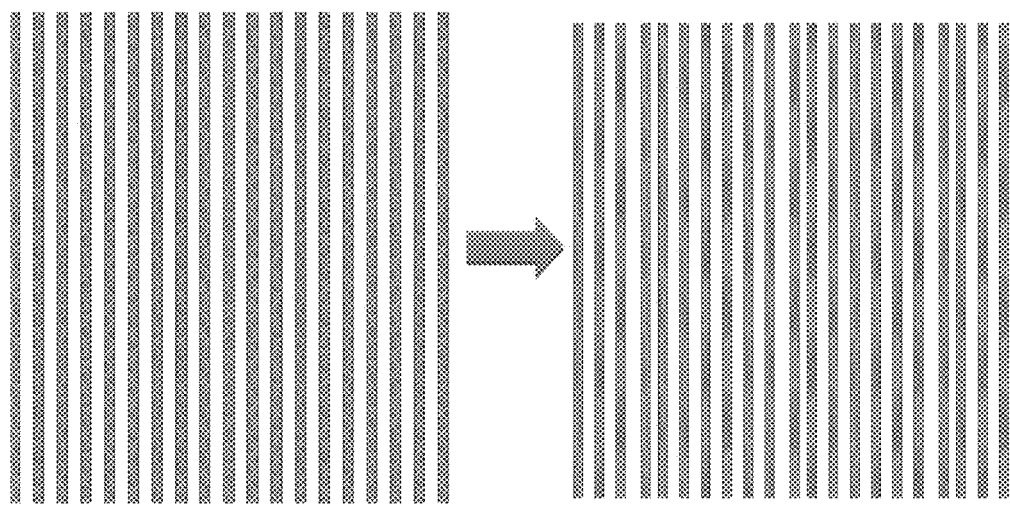
FIG. 9 shows pitch walking as a programmed defect in a mask pattern for generating a guidance pattern, as can be used in embodiments of the present disclosure.

FIG. 9 shows pitch walking as a programmed defect in a mask pattern for generating a guidance pattern. The CD remains constant and an offset is created in the pattern pitch. The magnitude of the offset is varied systematically from target to target.

Figure 10:
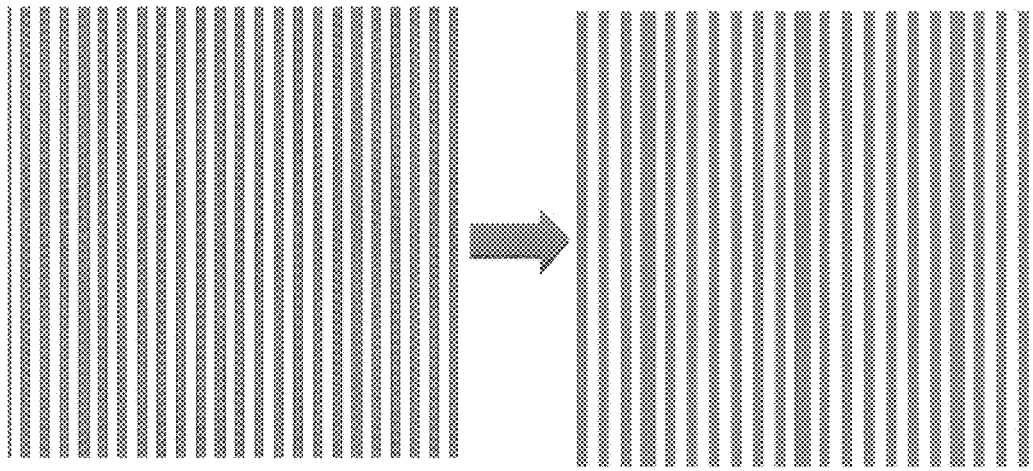
FIG. 10 shows local CD bias as a programmed defect in a mask pattern for generating a guidance pattern, as can be used in embodiments of the present disclosure.

FIG. 10 shows local CD bias as a programmed defect in a mask pattern for generating a guidance pattern. The defects may be introduced over a large section of the line or over smaller sections. Also the length of the section may be used as a parameter.

Figure 11:
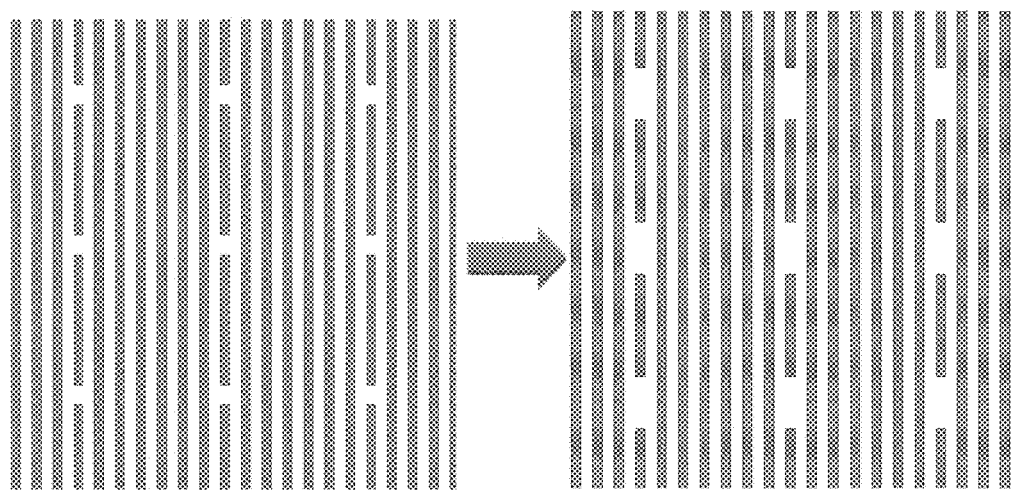
FIG. 11 shows gaps as a programmed defect in a mask pattern for generating a guidance pattern, as can be used in embodiments of the present disclosure.

FIG. 11 shows gaps as a programmed defect in a mask pattern for generating a guidance pattern. The size of the interruptions (gaps) in the line pattern (in this example in Y-direction) may be varied.

Figure 12:
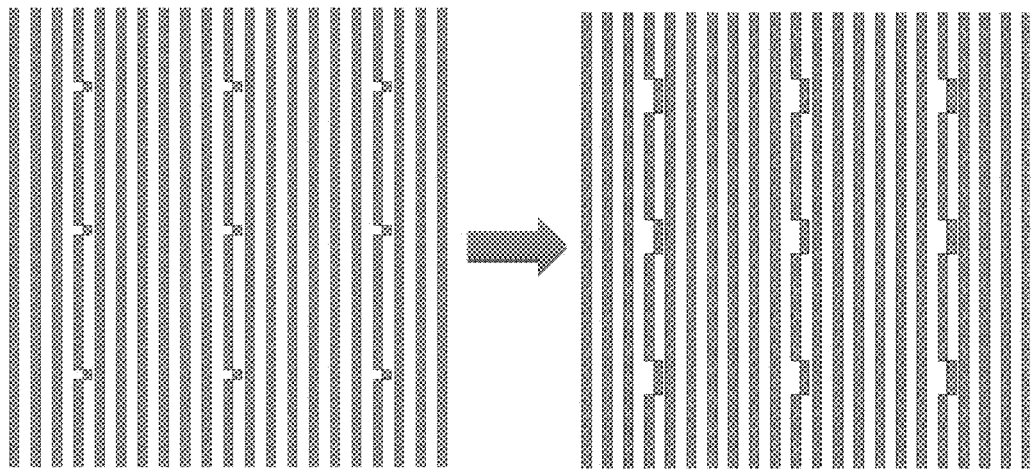
FIG. 12 shows notches as a programmed defect in a mask pattern for generating a guidance pattern, as can be used in embodiments of the present disclosure.

FIG. 12 shows notches as a programmed defect in a mask pattern for generating a guidance pattern. The defects may be introduced over a large section of the line or over smaller sections. Also the length of the section may be used as a parameter.

All programmed defects are used to investigate the ability of the BCP to heal defects in the patterns upon application of the DSA technique. Embodiments of the present disclosure allow to give a qualification score of the processing method to heal the defects in the resist for the different sets of programmed defects. Embodiments of the present disclosure allow to identify the defects that pertain to DSA and/or to identify the conditions for which the DSA technique is far less sensitive to defects in the pattern.

Other examples of process related defects include imperfections in the pre-patterns obtained in the lithography step, such as irregular critical dimension (CD) or line edge roughness (LER). Also here embodiments of the present disclosure facilitate investigation of the rectification capabilities of BCP materials and retrieval of the critical processing parameters that will result in defect formation.

In the example of FIGS. 9-12 the defects are positioned along the diagonal of the target from top left to bottom right. In other examples the defects may be distributed differently, where the density may be varied and the relative positioning of the defects may vary.

Through a scattered radiation pattern based technique it is possible to screen at which offset number the process breaks down and creates fingerprint patterns or less perfect alignment.

The effect each of the defects has on the quality of the DSA process can be evaluated. The number and position of induced defects over the target may be varied. Analysis of the patterning qualification score as a function of size, type, or number of defects gives information about the quality of the DSA materials and/or process. Embodiments of the present disclosure can be used to perform analysis on the effect a defect has on DSA gratings. This may help to facilitate the automation of the inspection process and to provide an objective qualification score. The inspection process is faster than conventional SEM inspection, and therefore may help to facilitate the scoring of more defect types/numbers with regard to the effect they have on the resulting DSA pattern.

According to particular embodiments of the present disclosure, the method may be adapted for evaluating the process window for a DSA technique. The block 210 may comprise obtaining a plurality of sets of parameter values for the parameterized set of processing steps and material properties. The plurality of sets of parameter values thereby span a process window for the DSA method. At block 220 the scattered radiation pattern technique is performed, and at block 230 a qualification score for each of the sets of parameters is obtained. At block 230 the process window for the DSA method is evaluated based on the qualification scores through the process window. Advantageously, the method also comprises normalization of the scattered radiation pattern results. Such normalisation may for example be performed based on SEM experiments.

In embodiments of the present disclosure the method comprises a step wherein the qualification score is compared with an earlier obtained qualification score. Both process windows were done with the same set of parameter values.

Figure 7:
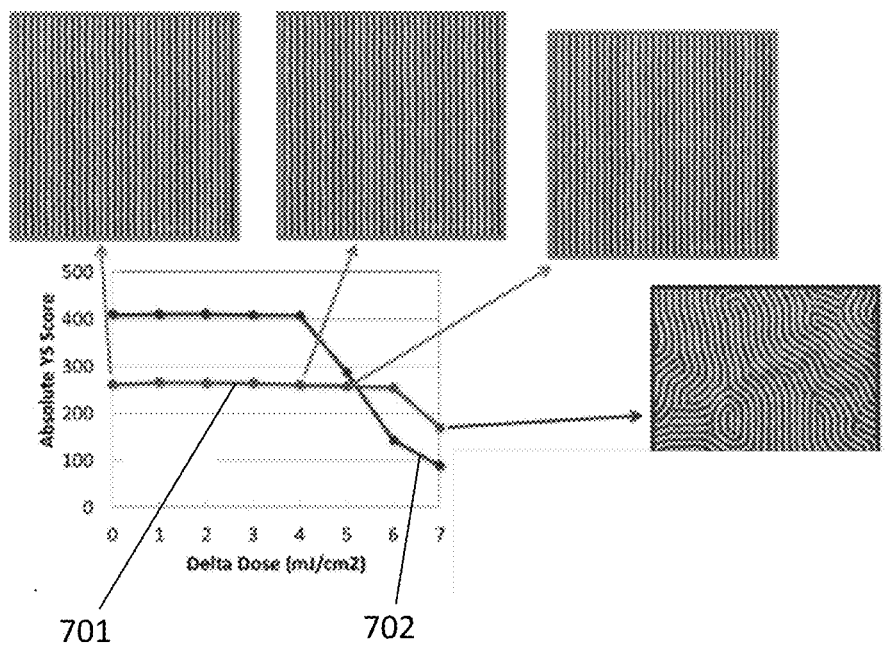
FIG. 7 shows a first and a second non-normalized qualification score of a first and a second wafer as a function of a dose, wherein the score is obtained using a method according to the present disclosure.
Figure 13:
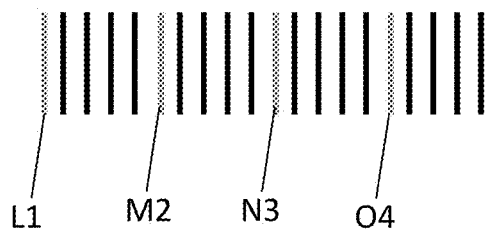
FIG. 13 illustrates a litho pre-pattern with programmed defects, as used in an example according to an embodiment of the present disclosure.
Figure 14:
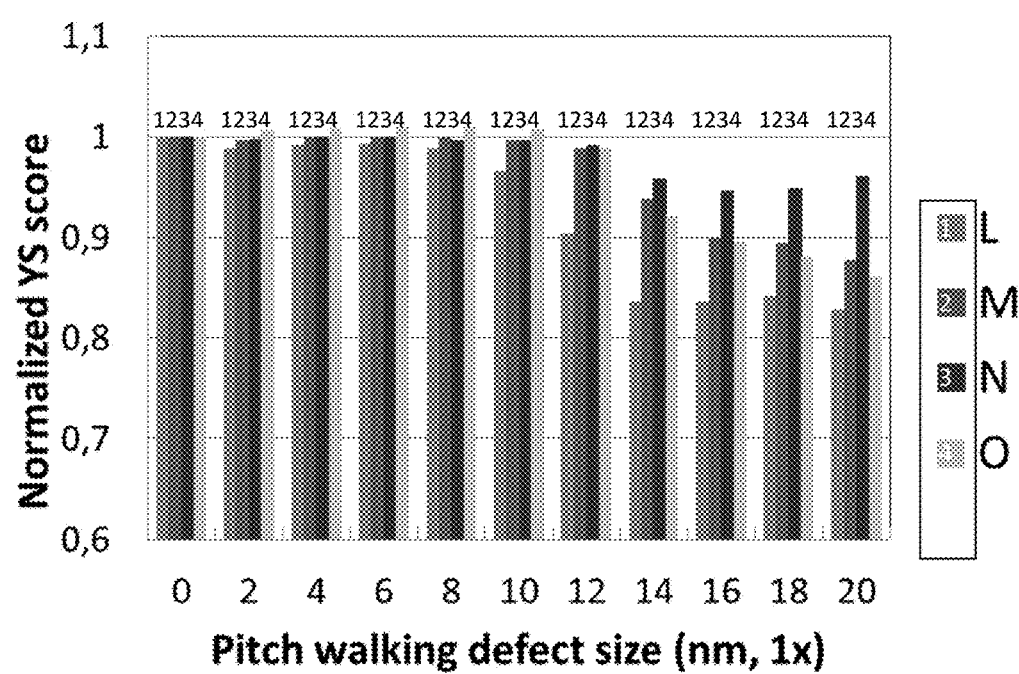
FIG. 14 illustrates a normalized score for the quality of the sample as a function of the pitch walking defect size (e.g., a number of times a 20 nm shift occurred) for four different samples, as used in an example according to an embodiment of the present disclosure.

Based on the comparison it is evaluated whether the DSA method has suffered from shifts in processing conditions or other conditions determining the outcome of the DSA method. In embodiments of the present disclosure the obtained qualification scores and corresponding parameter values are stored in a look up table. Comparing qualification scores is possible by browsing the look up table. Alternatively or in conjunction, comparison also may be performed using other algorithms. By way of example, embodiments of the present disclosure not limited thereto, experimental results indicative of features and advantages over the conventional methods are now discussed. The resilience of a number of samples against pitch walking defects was tested with the scattered pattern based technique. P90 litho pre-patterns were used with an increasing severeness of programmed pitch walking defects. Every fifth line of the lithographic pre-pattern was shifted by a multiple of 2 nm (2, 4, 6, and so forth). An example of a pre-pattern with pitch walking is shown in FIG. 13. The resilience was tested for 4 samples L1, M2, N3 and O4. FIG. 14 illustrates the normalized score when applying the scattered radiation pattern based technique. It can be seen that all samples deteriorate when the pitch walking defect size exceeds a certain size. Nevertheless, it can be concluded that the sample N3 is most resistant to programmed pitch walking defects, whereas the sample L1 is least resistant to pitch walking. By way of illustration, in FIG. 7 the qualification scores are obtained for a set of DSA patterns obtained by a DSA method wherein a different DSA dose is used for each DSA pattern. In the graph of FIG. 7 two curves are shown. A first curve 701 corresponds with a first wafer, and a second curve 702 corresponds with a second wafer. The SEM images of the first wafer are also shown. A high qualification score corresponds with high order in the SEM image and a low qualification score corresponds with low order in the corresponding SEM image. However it can be seen from FIG. 7 when comparing the first curve 701 and the second curve 702, that the terms high and low may only be valid within one wafer. Therefore, it may be difficult to interpret absolute scores and a proper normalisation is in the present example.

Figure 8:
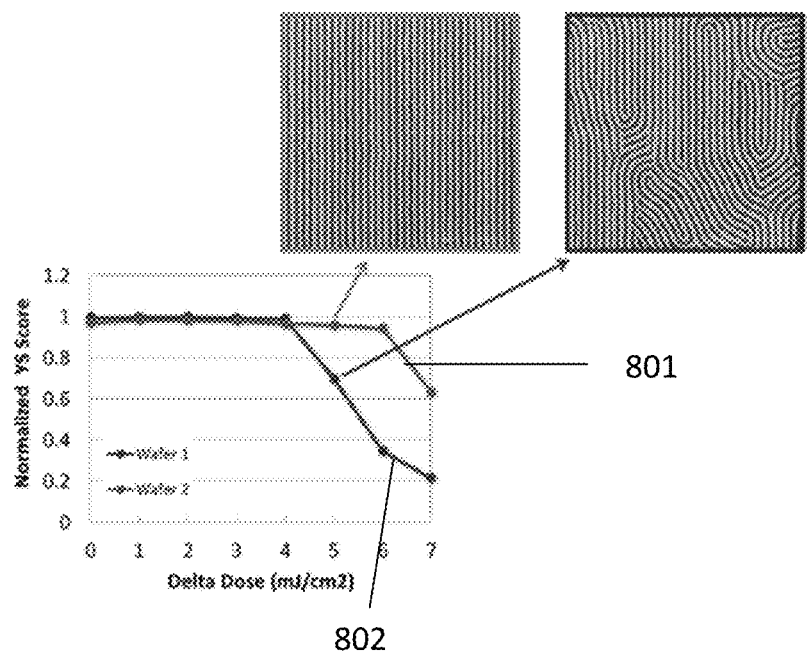
FIG. 8 shows the normalized qualification scores obtained using a method according to the present disclosure.

By way of illustration, such normalized curves are shown in FIG. 8. The qualification scores are normalized to 1 for a highly ordered SEM image. This normalisation is therefore done using an analysis of SEM measurements of the self-assembled patterns. The analysis of SEM measurements is only required for the normalization for 1 highly ordered SEM image. The remaining analysis can be done based on the automatically obtained normalised qualification score. After calibration of the qualification score the first curve 801 and the second curve 802 have the same value 1 for a highly ordered SEM image.

In a second aspect, the present disclosure relates to a system for storing a set of comparative data. The comparative data thereby correlates sets of parameter values and material properties with a qualification score. The parameter values are used for a parameterized set of processing steps and together with the material properties they characterize a DSA method. The qualification score is based on scattered radiation pattern results on a DSA pattern obtained using the DSA method characterized by the set of parameter values. Such a system may be a computing system or a memory system. The data may be stored in a look up table or in any other structured way linking the qualification score with an identification of a specific technique. In some embodiments the qualification score is based on scattered radiation pattern results obtained from a scattered radiation pattern technique on a DSA pattern obtained using the DSA method characterized by the set of parameter values and applied to a pattern comprising a number of induced defects. The latter allows for studying how sensitive a process is to defects and can be used for evaluating such techniques or for benchmarking. In some embodiments of the present disclosure the comparative data in the system is normalised based on scanning electron microscopy reference data.

In a third aspect, the present disclosure relates to a set of comparative data. The comparative data correlates sets of parameter values and material properties with a qualification score. The parameter values are used for a parameterized set of processing steps and together with the material properties they characterize a DSA method. The qualification score is based on scattered radiation pattern results obtained from a scattered radiation pattern technique on a DSA pattern obtained using the DSA method characterized by the set of parameter values. In some embodiments, the qualification score is based on scattered radiation pattern results obtained from a scattered radiation pattern technique on a DSA pattern obtained using the DSA method characterized by the set of parameter values and applied to a pattern comprising a number of induced defects.

In yet a further aspect, the present disclosure also relates to a method for evaluating a DSA method as described above implemented as a computer implemented processes or functions in a processor and to corresponding processors. One configuration of such a processor may for example include at least one programmable computing component coupled to a memory subsystem that includes at least one form of non-transitory memory, e.g., RAM, ROM, and so forth. It is to be noted that the computing component or computing components may be a general purpose, or a special purpose computing component, and may be for inclusion in a device, e.g., a chip that has other components that perform other functions. Thus, one or more aspects of the present disclosure can be implemented in digital electronic circuitry, or in computer hardware, firmware, software, or in combinations thereof. For example, each of the method elements or processes may be a computer-implemented element or process. Thus, while a processor as such is known, a system that includes the instructions to implement aspects of the method for evaluating a DSA method is not.

The present disclosure thus also includes a computer program product which provides the functionality of any of the methods according to the present disclosure when executed on a computing device.

In another aspect, the present disclosure relates to a data carrier for carrying a computer program product for evaluating a DSA method according to an embodiment as described above. Such a data carrier may comprise a computer program product tangibly embodied thereon and may carry machine-readable code for execution by a programmable processor. The present disclosure thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

What is claimed is:

1. A method for evaluating the quality of a directed self-assembling method used for generating directed self-assembling patterns, the method comprising:
   obtaining at least one set of parameter values for a parameterized set of processing steps and material properties characterizing the directed self-assembling method, thus characterizing a specific directed self-assembling method used for generating a directed self-assembled layer;
   obtaining, using a scatterometer, a scattered radiation pattern on the directed self-assembled layer, wherein the directed self-assembled layer is obtained by applying the directed self-assembling method characterized by the set of parameter values on a guiding pattern comprising a number of induced, intended defects, thus obtaining scattered radiation pattern results for the directed self-assembled pattern; and
   determining, using a computing device and based on the scattered radiation pattern results, a qualification score identifying a robustness of the directed self-assembling method to the induced, intended defects in the guiding pattern and correlating the qualification score with the set of parameter values.

2. The method according to claim 1, wherein the induced, intended defects include one or more of non-local or local pitch offsets, interruptions in the line patterns, or local or non-local CD bias.

3. The method according to claim 1, wherein the induced, intended defects have a tuned defect size.

4. The method according to claim 1, wherein the induced, intended defects are systematically distributed and/or are randomly distributed.

5. The method according to claim 1, further comprising:
   obtaining a plurality of sets of parameter values for the parameterized set of processing steps and material properties, wherein the plurality of sets of parameter values span a process window for the directed self-assembling method;
   performing the steps of obtaining a scattered radiation pattern and determining a qualification score for each of the sets of parameters; and
   evaluating the process window for the directed self-assembling method based on the obtained qualification scores through the process window.

6. The method according to claim 1, wherein determining based on the scattered radiation pattern results a qualification score further comprises performing a normalization of the scattered radiation pattern results.

7. The method according to claim 6, wherein performing the normalization further comprises normalizing the scattered radiation pattern results using an analysis of scanning electron microscopy measurements of the self-assembled layers.

8. The method according to claim 1, wherein the method further comprises:
comparing the qualification score correlated with the set of parameters with a qualification score obtained earlier in time for the set of parameter values; and
evaluating, based on the comparing, whether the directed self-assembling method needs to be amended.

9. The method according to claim 8, wherein comparing the qualification score further comprises a comparison with a reference comprising previously recorded qualification scores correlated with specific sets of parameter values.

10. The method according to claim 1, wherein the method comprises obtaining the directed self-assembled layer by applying the directed self-assembling method characterized by the set of parameter values on the guiding pattern comprising the number of induced, intended defects.

11. A computer program product for, when run on a processing unit, performing a method for evaluating according to claim 1.

12. A data carrier comprising a computer program product according to claim 11.

13. A transmission of a computer program product according to claim 11 over a local or wide area network.

14. The method according to claim 1, wherein the scatterometer is an angle-resolved polarized reflectometry based scatterometer.

15. A system comprising:
a scatterometer, configured to obtain a scattered radiation pattern;
a storage; and
a computing device that executes instructions so as to carry out operations, the operations comprising:
causing the scatterometer to obtain a scattered radiation pattern, wherein the scattered radiation pattern comprises radiation scattered from a directed self-assembly layer, wherein the directed self-assembled layer is obtained by applying a directed self-assembling method on a guiding pattern comprising a number of induced, intended defects;
determining, based on the scattered radiation pattern, a qualification score, wherein the qualification score is indicative of an order of the directed self-assembled layer;
comparing the qualification score and at least one set of parameter values indicative of a parameterized set of processing steps and material properties characterizing the directed self-assembling method; and
storing comparative data in the storage, wherein the comparative data is based on the comparison.

16. The system according to claim 15, wherein the comparative data is normalised based on scanning electron microscopy reference data.

17. The system according to claim 15, wherein the scatterometer is an angle-resolved polarized reflectometry based scatterometer.

18. A non-transitory computer-readable medium having stored therein instructions, that when executed by a processor, cause the processor to perform functions comprising:
obtaining at least one set of parameter values for a parameterized set of processing steps and material properties characterizing the directed self-assembling method, thus characterizing a specific directed self-assembling method used for generating a directed self-assembled layer;
obtaining a scattered radiation pattern on the directed self-assembled layer, wherein the directed self-assembled layer is obtained by applying the directed self-assembling method characterized by the set of parameter values on a guiding pattern comprising a number of induced, intended defects, thus obtaining scattered radiation pattern results for the directed self-assembled pattern, and wherein the scattered radiation pattern is obtained using a scatterometer; and
determining, using a computing device and based on the scattered radiation pattern results, a qualification score identifying a robustness of the directed self-assembling method to the induced, intended defects in the guiding pattern and correlating the qualification score with the set of parameter values.

* * * * *